US012755341B2

(12) United States Patent
Osumi

(10) Patent No.: US 12,755,341 B2
(45) Date of Patent: Oct. 6, 2026

(54) ULTRASONIC DIAGNOSTIC SYSTEM AND ULTRASOUND IMAGE PROCESSING METHOD

(71) Applicant: Canon Kabushiki Kaisha, Tokyo (JP)

(72) Inventor: Ryota Osumi, Nasushiobara (JP)

(73) Assignee: Canon Kabushiki Kaisha, Tokyo (JP)

( * ) Notice: Subject to any disclaimer, the term of this patent is extended or adjusted under 35 U.S.C. 154(b) by 449 days.

(21) Appl. No.: 17/643,461

(22) Filed: Dec. 9, 2021

(65) Prior Publication Data

US 2022/0188998 A1 Jun. 16, 2022

(30) Foreign Application Priority Data

Dec. 11, 2020 (JP) ................................ 2020-206013

(51) Int. Cl.

| | |
|---|---|
| ***G06T 5/00*** | (2024.01) |
| ***A61B 8/00*** | (2006.01) |
| ***A61B 8/08*** | (2006.01) |
| ***G06T 5/20*** | (2006.01) |
| ***G06T 5/50*** | (2006.01) |
| ***G06T 5/70*** | (2024.01) |
| ***G06T 5/73*** | (2024.01) |
| ***G16H 50/20*** | (2018.01) |

(52) U.S. Cl.

CPC ................ *G06T 5/50* (2013.01); *A61B 8/463* (2013.01); *G06T 5/20* (2013.01); *G06T 5/70* (2024.01); *G06T 5/73* (2024.01); *G16H 50/20* (2018.01); *G06T 2200/24* (2013.01); *G06T 2207/10132* (2013.01); *G06T 2207/20224* (2013.01)

(58) Field of Classification Search

CPC ....... G06T 2200/24; G06T 2207/10132; G06T 2207/20224

See application file for complete search history.

(56) References Cited

U.S. PATENT DOCUMENTS 7,593,603 B1 * 9/2009 Wilensky ................. G06T 5/00 382/311
2009/0171208 A1 7/2009 Osumi et al.

(Continued)

FOREIGN PATENT DOCUMENTS

| | | |
|---|---|---|
| JP | 2009-153918 A | 7/2009 |
| JP | 2009-233408 A | 10/2009 |
| JP | 2015-100539 A | 5/2015 |

OTHER PUBLICATIONS

Reference V, W, X are a single reference, broken down into separate form fields because of its lengthy URL.*

(Continued)

*Primary Examiner* — Irete F Ehichioya
*Assistant Examiner* — Samuel Shen
(74) *Attorney, Agent, or Firm* — Oblon, McClelland, Maier & Neustadt, L.L.P.

(57) ABSTRACT

An ultrasound diagnosis system according to an embodiment includes processing circuitry. The processing circuitry generates two or more images derived from image processing performed on an ultrasound image relating to a subject. The processing circuitry generates two or more adjusted derived images by applying variable coefficients to each of the two or more derived images. The processing circuitry generates a synthesized image of the ultrasonic image and the two or more adjusted derived images.

15 Claims, 10 Drawing Sheets

(56) References Cited

U.S. PATENT DOCUMENTS

| | | | | |
|---|---|---|---|---|
| 2013/0271455 | A1* | 10/2013 | Tsujita | G06T 5/75 345/419 |
| 2019/0000414 | A1* | 1/2019 | Honjo | A61B 8/085 |
| 2019/0066346 | A1* | 2/2019 | Ye | G06T 11/006 |
| 2019/0138838 | A1* | 5/2019 | Liu | G06T 3/4053 |
| 2019/0261956 | A1* | 8/2019 | Srinivasan | G01S 7/003 |
| 2020/0286214 | A1* | 9/2020 | Kaneko | G06T 11/003 |
| 2021/0027292 | A1* | 1/2021 | Farivar | G06F 18/24 |

OTHER PUBLICATIONS

Kang, Jinbum. "A New Feature-enhanced Speckle Reduction Method based on Multiscale Analysis and synthesis for Ultrasound B-mode Imaging" [published Nov. 29, 2018], [online], [retrieved on Apr. 17, 2024]. Retrieved from the internet <URL: https://www.researchgate.net/profile/Jinbum-Kang/publication/286562739_A_new_feature-enhanced_speckle_reduction_method_based_on_multiscale_analysis_and_synthesis_for_ultrasound_B-mode_imaging/links/5bff9a1145851523d15343e3/A-new-feature-enhanced-speckle-reduction-method-based-on-multiscale-analysis-and-synthesis-for-ultrasound-B-mode-imaging.pdf > (Year: 2018).*

Northan, B. "Image compression with a multiresolution neural network" [published Dec. 26, 2006], [online], [retrieved on Mar. 9, 2025]. Retrieved from the internet <URL: https://ieeexplore.ieee.org/abstract/document/4028884 > (Year: 2006).*

Japanese Office Action issued Jun. 11, 2024 in Japanese Patent Application No. 2020-206013, 5 pages.

* cited by examiner

ULTRASONIC DIAGNOSTIC SYSTEM AND ULTRASOUND IMAGE PROCESSING METHOD

CROSS-REFERENCE TO RELATED APPLICATIONS

This application is based upon and claims the benefit of priority from Japanese Patent Application No. 2020-206013, filed Dec. 11, 2020, the entire contents of which are incorporated herein by reference

FIELD

Embodiments described herein relate generally to an ultrasonic diagnostic system and an ultrasound image processing method.

BACKGROUND

As a technique of image processing in ultrasonic diagnosis, there is a known method of controlling multiresolution high pass signals, the method including performing multiresolution decomposition on an ultrasound image, applying a nonlinear anisotropic diffusion filter or a coherence enhancing diffusion (CED) filter to each decomposed image, and using edge information obtained during the filtering process. In this technique, the edge information in each layer (spatial map indicating tissue boundaries) is also used to distinguish between an area where noise or speckling should be reduced and an area where smoothing along or emphasizing of tissue boundaries should be performed.

The nonlinear anisotropic diffusion filter adopted in this technique has a few parameters for controlling a strength of a filter, which is dependent on the direction of a tissue boundary and an extent of a detected edge, and such parameters are prepared for each layer of multiresolution decomposition; therefore, the number of parameters tends to be large. Although a large number of parameters allows an image quality architect to fine-tune an image quality of a filter, it is difficult to quickly reach a desired image quality unless the image quality architect is adept at manipulating the filter.

DETAILED DESCRIPTION

An ultrasound diagnosis system according to an embodiment includes processing circuitry. The processing circuitry generates two or more images derived from image processing performed on an ultrasound image relating to a subject. The processing circuitry generates two or more adjusted derived images by applying variable coefficients to each of the two or more derived images. The processing circuitry generates a synthesized image of the ultrasound image and the two or more adjusted derived images.

Hereinafter, embodiments of an ultrasonic diagnostic system and an ultrasound image processing method will be explained in detail with reference to the accompanying drawings.

FIRST EMBODIMENT

Figure 1:
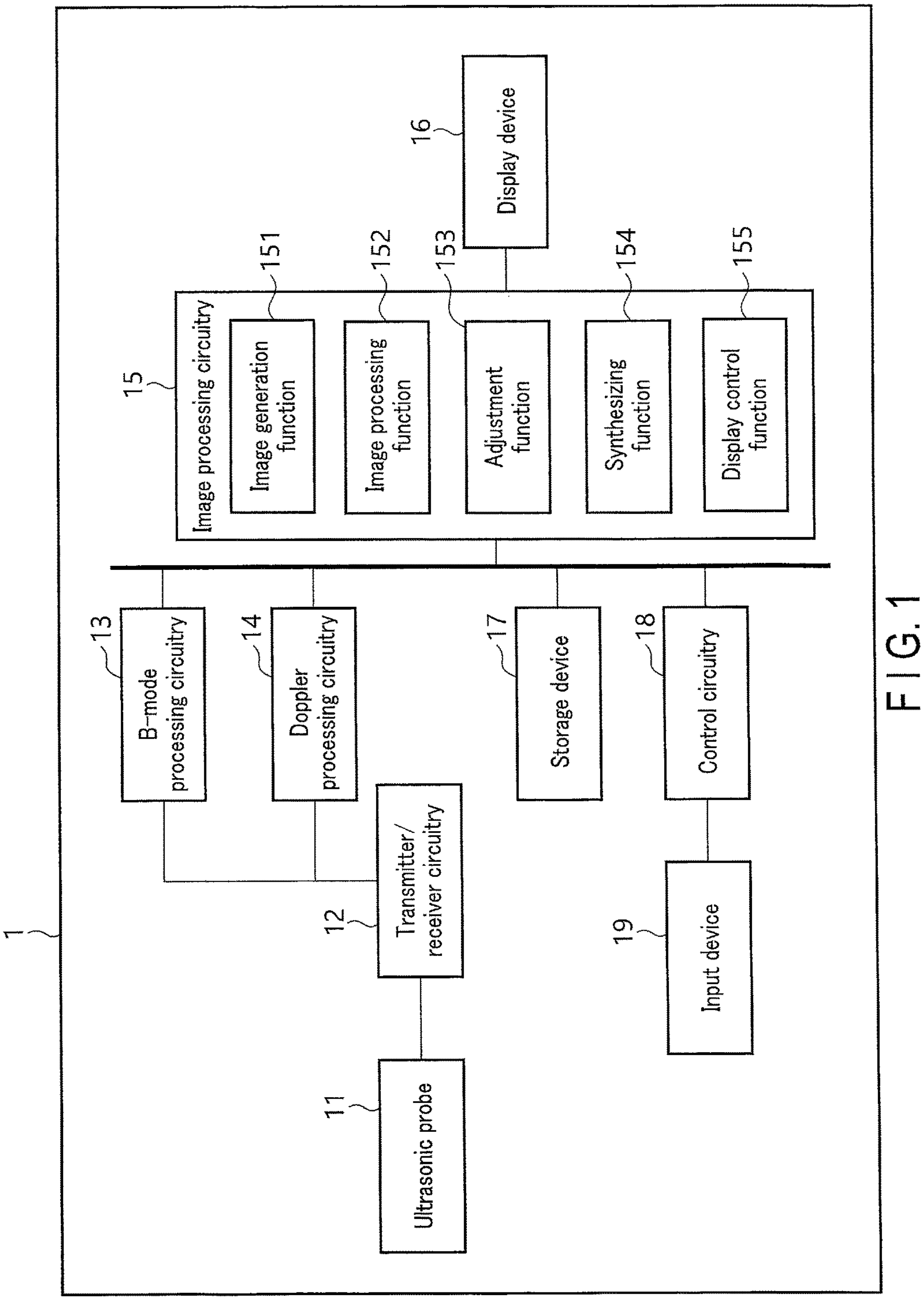
FIG. 1 is a diagram showing an example configuration of an ultrasonic diagnostic system according to a first embodiment.

FIG. 1 is a diagram showing an example configuration of an ultrasonic diagnostic system 1 according to a first embodiment. As shown in FIG. 1, the ultrasonic diagnosis system 1 includes an ultrasonic probe 11, transmitter/receiver circuitry 12, B-mode processing circuitry 13, Doppler processing circuitry 14, image processing circuitry 15, a display device 16, a storage device 17, control circuitry 18, and an input device 19.

The ultrasonic probe 11 is a device (probe) that takes charge of transmitting and receiving ultrasonic waves emitted from and reflected on a subject, and consists of an electrical/mechanical reversible sensing element. The ultrasonic probe 11 is composed of, for example, a phased-array type probe whose distal end is equipped with a plurality of elements arranged in an array. It is thereby possible for the ultrasonic probe 11 to convert a pulse drive voltage of a supplied driving signal to an ultrasonic pulse signal and transmit it in a desired direction within a scan region of a subject and to convert the ultrasonic signal reflected from the subject to an echo signal of a corresponding voltage.

For the ultrasonic signal transmission, the transmitter/receiver circuitry 12 supplies a driving signal to the ultrasonic probe 11. Specifically, the transmitter/receiver circuitry 12 has trigger generating circuitry, delay circuitry, and pulser circuitry, and the like. The pulser circuitry repeatedly generates rate pulses for forming transmission ultrasonic waves at a predetermined rate frequency. The delay circuitry provides each rate pulse generated by the pulser circuitry with a delay time for each piezoelectric oscillator, which is necessary for converging ultrasound generated by the ultrasonic probe 11 in a beam form and determining transmission directivity. The trigger generating circuitry supplies driving signals (driving pulses) to the ultrasonic probe 11 at a timing based on the rate pulse. In other words, by varying the delay time provided to each rate pulse, the delay circuitry adjusts a direction of a transmission from the piezoelectric oscillator surface as appropriate.

The transmitter/receiver circuitry 12 has a function of changing a transmit frequency and a transmit drive voltage, etc. instantaneously based on an instruction from the processing circuitry 18 so that a predetermined scan sequence can be performed. In particular, the change of a transmit drive voltage is realized by an origination circuit capable of instantaneously switching the voltage value, or a mechanism for electrically switching one power source unit to another.

For the ultrasonic signal reception, the transmitter/receiver circuitry 12 executes various types of processing on the reflected echo signals in accordance with a reflected wave signal received by the ultrasonic probe 11 and converts the echo signal to reflected wave data in accordance with reception directivity. Specifically, the transmitter/receiver circuitry 12 has an amplifier circuit, an A/D converter, and an adder, etc. The amplification circuitry executes gain correction processing for each channel by amplifying reflected wave signals. The A/D converter performs A/D conversion on a gain-corrected reflected wave signal and gives digital data a delay time required for determining reception directivity. The adder adds up A/D-converted reflected wave signals and generates reflected wave data. By the adding process of the adder, a reflected component is enhanced in a direction corresponding to the reception directivity of the reflected wave signal.

The B-mode processing circuitry 13 performs logarithmic amplification, envelope detection processing, and logarithmic compression, etc. on the reflected wave data from the transmitter/receiver circuitry 12 and generates B-mode information in which a signal strength at each sample point is expressed in a luminance level.

The Doppler processing circuitry 14 performs a color Doppler technique on the reflected wave data from the transmitter/receiver circuitry 12 and calculates blood flow information, namely Doppler information. With the color Doppler technique, the ultrasonic transmission and reception is performed on the same scanning line multiple times, and an MTI (moving target indicator) filter is applied to data columns of the same position in order to inhibit signals (clutter signals) originating from a static tissue or slow-moving tissue and extract signals originating from blood flow. Furthermore, with the color Doppler technique, Doppler information, such as a blood flow rate, blood flow dispersion, and blood flow power, etc., is estimated from these blood flow signals.

The image processing circuitry 15 is a processor performing image processing. The image processing circuitry 15 executes a program stored in the memory apparatus 17 to realize a function corresponding to the program. The image processing circuitry 15 realizes, for example, an image generation function 151, an image processing function 152, an adjustment function 153, a synthesizing function 154, and a display control function 155. The image generation function 151, the image processing function 152, the adjustment function 153, the synthesizing function 154, and the display control function 155 are not necessarily realized by a single image processing circuitry 15; they may be realized by multiple image processing circuitries 15 in conjunction. The image generation synthesizing function 151, the image processing function 152, the adjustment function 153, the synthesizing function 154, and/or the display control function 155 may be implemented as hardware, not as a program.

Through the realization of the image generation function 151, the image processing circuitry 15 converts the scanning scheme of the B-mode information to a scanning scheme suitable for displaying (scanning conversion), and generates a B-mode image of a subject. Similarly, the image processing circuitry 15 converts the scanning method of the Doppler information to a scanning method suitable for display (scanning conversion) and generates a Doppler image of a subject. Display images such as a B-mode image and a Doppler image will be collectively called "ultrasound images". The image processing circuitry 15 also generates, together with the ultrasound images, information indicating compositing, parallel arrangement, or display position of each image information item, and various kinds of information used to assist the operation of the ultrasonic diagnostic system 1, and attendant information required for ultrasonic diagnosis such as patient information.

Through the realization of the image processing function 152, the image generation circuitry 15 generates two or more derived images derived from image processing performed on an ultrasound image generated by the image generation function 151. Specifically, the image processing circuitry 15 generates two or more derived images representing two or more image characteristics to be processed through an application of the above-mentioned image processing on an ultrasound image based on a first output image generated by performing the image processing on the ultrasound image, a second output image generated by applying the image processing on the ultrasound image when parameters used for the image processing are set to predetermined values, and an ultrasound image. This image processing is nonlinear image processing performed to improve image quality through reduction of noise or speckles included in an ultrasound image, smoothing along a tissue boundary, and emphasizing of tissue boundaries. As the image processing, nonlinear image filtering using a diffusion equation is performed. The parameters are those relating to a diffusion tensor of a diffusion equation. In the first embodiment, the image processing circuitry 15 generates two or more derived images by applying a nonlinear image filter to an ultrasound image.

Through the realization of the adjustment function 153, the image processing circuitry 15 generates two or more adjusted derived images by applying variable coefficient values to each of the two or more derived images generated by the image processing function 152. The derived images to which a coefficient value is applied will be called "adjusted derived images".

Through the realization of the synthesizing function 154, the image processing circuitry 15 generates a synthesized image by synthesizing an ultrasound image targeted for the processing by the image processing function 152 with two or more adjusted derived images generated by the adjustment function 153.

Through realization of the display control function 155, the processing circuitry 15 outputs various information items via the display device 16. For example, the image processing circuitry 15 displays the synthesized image generated by the synthesizing function 154 on the display device 16.

The display device 16 is a device that displays visual video information converted from display information provided from the image processing circuitry 15, in conjunction with the image processing circuitry 15. For example, the display device 16 displays a synthesized image generated by the image processing circuitry 15. As the display device 16, a CRT display, a liquid crystal display, an organic EL display, and a plasma display are applicable for example. A projector may be provided as the display device 16.

The storage circuitry 17 is a type of storage such as a ROM (read only memory), a RAM (random access memory), an HDD (Hard Disk Drive), an SSD (Solid State Drive), or an integrated circuit storage device, etc. which stores various types of information. The storage device 17 may also be, for example, a drive that performs reading and writing of various kinds of information on a portable storage medium such as a CD-ROM drive, a DVD drive, or a flash memory. For example, the storage device 17 stores various types of information, such as B-mode information, Doppler information, a B-mode image, a Doppler image, and a synthesized image, etc.

The control circuitry 18 is a processor that controls all of the processing in the ultrasonic diagnostic system 1. The control circuitry 18 executes a program stored in the memory apparatus 17 to realize a function corresponding to the program. Specifically, the control circuitry 18 controls the processing in the transmitter/receiver circuitry 12, the B-mode processing circuitry 13, the Doppler processing circuitry 14, and the image processing circuitry 15, based on various setting requests that are input by an operating person via an input device 19, various control programs, and various types of data. Furthermore, the control circuitry 18 includes a function to interface with the input device 19.

The input device 19 serves as various types of user interfaces on a touch panel or an operation panel. An operating person can input various operations and commands to the ultrasonic diagnostic system 1 via the input device 19. The display device 16 and the input device 19 are not necessarily separated and they may be integrated as a mechanism.

The transmitter/receiver circuitry 12, the B-mode processing circuitry 13, the Doppler processing circuitry 14, the image processing circuitry 15, the display device 16, the storage device 17, the control circuitry 18, and the input device 19 are packaged in a single housing that may be called an apparatus main body, and the ultrasonic probe 11 is detachably connected to the apparatus main body via a cable. The hardware configuration of the ultrasonic diagnostic system 1 is not limited to the above. For example, the functions of the transmitter/receiver circuitry 12, the B-mode processing circuitry 13, the Doppler processing circuitry 14, the image processing circuitry 15, the display device 16, the storage device 17, the control circuitry 18, and the display device 19 may be partially or entirely implemented in the ultrasonic probe 11. The functions of the image processing circuitry 15, the display device 16, and the storage device 17 may be partially or entirely implemented in a computer connected to the apparatus main body via a network. The image processing circuitry 15 and the control circuitry 18 are not necessarily implemented in separate hardware and may be implemented in a single piece of hardware.

Next, the processing in the image processing circuitry 15 according to the first embodiment will be described in detail. The image processing circuitry 15 can perform either a nonlinear anisotropic diffusion filter or a coherence emphasis diffusion filter as an example of a nonlinear image filter. These nonlinear image filters reduce noise or speckles included in an ultrasound image and perform smoothing along and emphasizing of tissue boundaries.

First, details of the nonlinear image filter are described. Hereinafter, as an example, suppose a nonlinear anisotropic diffusion filter is performed as a nonlinear image filter. In addition, suppose that an ultrasound image to which the nonlinear image filter is applied is a B-mode image. A B-mode image to which the nonlinear image filter is applied may be an image either before or after scan conversion is performed by the image processing circuitry 15. This B-mode image may be either an image to which gain adjustment is made in accordance with a depth position, such as time gain control (TGC), etc., or an image to which gain adjustment is not made.

Figure 2:
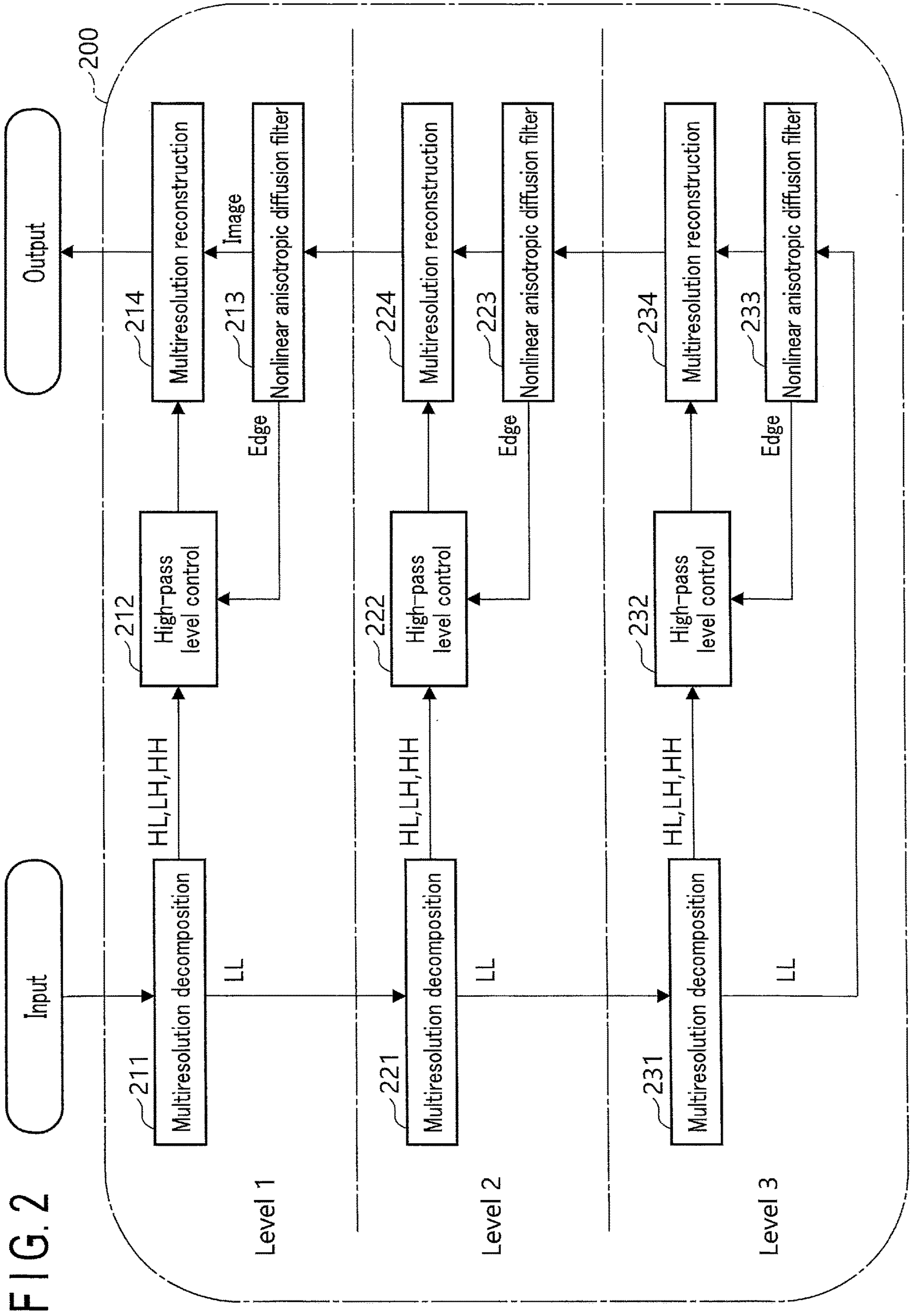
FIG. 2 is a diagram showing a typical flow of a nonlinear image filter by an image processing function of image processing circuitry according to the first embodiment.

FIG. 2 is a diagram showing a typical flow of a nonlinear image filter 200A by the image processing function 152 of the image processing circuitry 15. The nonlinear image filter 200A has a multiplex structure consisting of multiple layers so that multiresolution decomposition/reconstruction can be performed. In the present embodiment, the highest order of the multiresolution decomposition/reconstruction is level 3. The highest order is not limited to level 3, as long as it is 2 or higher.

The nonlinear image filter 200A has, for each level, a multiresolution decomposition process (211, 221, and 231), a nonlinear anisotropic diffusion filter process (213, 223, and 233), a high-pass level control process (212, 222, and 232), and a multiresolution reconstruction process (214, 224, and 234).

The multiresolution decomposition processes 211, 221, and 231 at respective levels perform multiresolution decomposition on an input image. For the multiresolution decomposition processes 211, 221, and 231, various techniques, such as discrete wavelet transformation and a Laplacian pyramid method, are possible. As a result of multiresolution decomposition of a two-dimensional image, the decomposed image is divided into a low-pass image (LL), a horizontal direction high-pass image (LH), a vertical direction high-pass image (HL), and a diagonal direction high-pass image (HH), in each of which the length and width (number of pixels) are a half of those before the decomposition.

The multiresolution decomposition process 211 at level 1 performs multiresolution decomposition on a B-mode image generated by the image generation function 151 to generate a low-pass image, a horizontal-direction high-pass image, a vertical-direction high-pass image, and a diagonal-direction high-pass image of level 1. The multiresolution decomposition process 221 and 231 at level 2 and level 3 performs a multiresolution decomposition process on a low-pass image generated by the multiresolution decomposition process 211 and 221 at a preceding layer to generate a low-pass image, a horizontal-direction high-pass image, a vertical-direction high-pass image, and a diagonal-direction high-pass image of each level.

The nonlinear anisotropic diffusion filter process 213, 223, or 233 at each level applies a nonlinear anisotropic diffusion filter to a low-pass image generated in the multiresolution decomposition process 211, 221, and 231 at the corresponding level and generates a filtered low-pass image. The nonlinear anisotropic diffusion filter processes 213, 223, and 233 outputs edge information based on the low-pass image. Edge information is information regarding a size and a direction of an edge.

Herein, the nonlinear anisotropic diffusion filter is described in detail. The nonlinear anisotropic diffusion filter is expressed in the following partial differential equation (1):

$$\frac{\partial I}{\partial t} = div[D\nabla I] \tag{1}$$

Herein, I is a pixel value of an image to be processed, ∇I is its gradient vector, and t is a time relating to the processing. In the actual processing, t represents the number of times of processing performed with this diffusion equation. Although the times t may be any number of times in the present embodiment, suppose t is 1 for the sake of explanation.

D in the equation (1) represents a diffusion tensor which can be expressed as the equation (2) below:

$$D = \begin{pmatrix} d_{11} & d_{12} \\ d_{12} & d_{22} \end{pmatrix} = R\begin{pmatrix} \lambda_1 & 0 \\ 0 & \lambda_2 \end{pmatrix}R^T = R^T\begin{pmatrix} c_1 & 0 \\ 0 & c_2 \end{pmatrix}R \quad (2)$$

$\lambda_1$ and $\lambda_{D2}$ in the equation (2) are unique values of the diffusion tensor D, and R is a unique vector of the diffusion tensor D. R represents a rotation matrix. R is expressed by $R=(\omega_1, \omega_2)$ based on the unique vectors $\omega_1$ and $\omega_2$ of the diffusion tensor D.

The diffusion tensor D gives a computing operation to multiply coefficients $c_1$ and $c_2$ respectively with a specific direction and a direction perpendicular thereto of a gradient vector of each pixel. A specific direction is a direction of an edge of a structure such as tissue drawn on an image, and the coefficient is dependent on the size of the edge.

To detect the size and direction of an edge, a structure tensor of the image is determined and its unique value and vector are calculated. The unique value is associated with the size of an edge, and the unique vector represents the direction of an edge.

The structure tensor S is expressed as the equation (3) below.

$$S = G_\rho * \begin{pmatrix} I_x^2 & I_xI_y \\ I_xI_y & I_y^2 \end{pmatrix} = \begin{pmatrix} G_\rho * I_x^2 & G_\rho * (I_xI_y) \\ G_\rho * (I_xI_y) & G_\rho * I_y^2 \end{pmatrix} = \begin{pmatrix} s_{11} & s_{12} \\ s_{12} & s_{Z2} \end{pmatrix} = R\begin{pmatrix} \mu_1 & 0 \\ 0 & \mu_2 \end{pmatrix}R^T \quad (3)$$

$I_x$ represents a spatial differential of the image I in an x direction (horizontal direction), and $I_y$ represents a spatial differential of the image I in a y direction (vertical direction). $G_\rho$ represents a two-dimensional Gaussian function, and an operator "*" represents convolution. The unique values $\mu_1$ and $\mu_2$ are a first unique value and a second unique value of a two-dimensional structure tensor S. R is a rotation matrix consisting of unique vectors of the structure tensor S.

The edge information of the structure tensor S is used to calculate the diffusion tensor D. First, the size E of the edge is dependent on the difference between the first unique value $\mu_1$ and the second unique value $\mu_2$ and is calculated by, for example, the following equation (4):

$$E = 1 - \exp\left(-\frac{(\mu_1 - \mu_2)^2}{k^2}\right) \quad (4)$$

The parameter k is a parameter indicating a degree of extraction of an edge component. The parameter k can be discretionarily set by a user via the input device 19, etc. For example, if the parameter k is set to be small, the edge component is more easily extracted.

Furthermore, the coefficient $c_1$ used in the diffusion tensor D becomes the function $f_1$ of the edge size E by the following equation (5), and the coefficient $c_2$ becomes the function $f_2$ of the edge size E by the following equation (6):

$$c_1 = f_1(E) \quad (5)$$

$$c_2 = f_2(E) \quad (6)$$

The direction of the edge corresponds to the rotation matrix R. Each element value $d_{11}$, $d_{12}$, and $d_{22}$ is calculated by the above equation (2) based on the coefficient $c_1$, the coefficient $c_2$, and the rotation matrix R.

The calculation of the edge size and direction does not have to strictly follow the above-described method; rather, a sobel filter, a Gabor filter, or a high-pass component of multiresolution decomposition may be applied, instead of calculating $I_x$ and $I_y$ as the first step of the process.

The equations (5) and (6) actually are a linear polynomial of the edge size E; therefore, about four parameters for controlling the coefficients $c_1$ and $c_2$ are required.

The calculation of the nonlinear anisotropic diffusion filter is conducted by a numerical analysis solution of a partial differential equation in accordance with the equation (1) above. In other words, at time t, a new pixel value of a point at time t+Δt is calculated based on each pixel value of nine pixels, which consist of a certain pixel and eight pixels around it, and element values $d_{11}$, $d_{12}$, and $d_{22}$ of the diffusion tensor D, and subsequently the same calculation is repeated once to a few times, using t+Δt as a new t.

Figure 3:
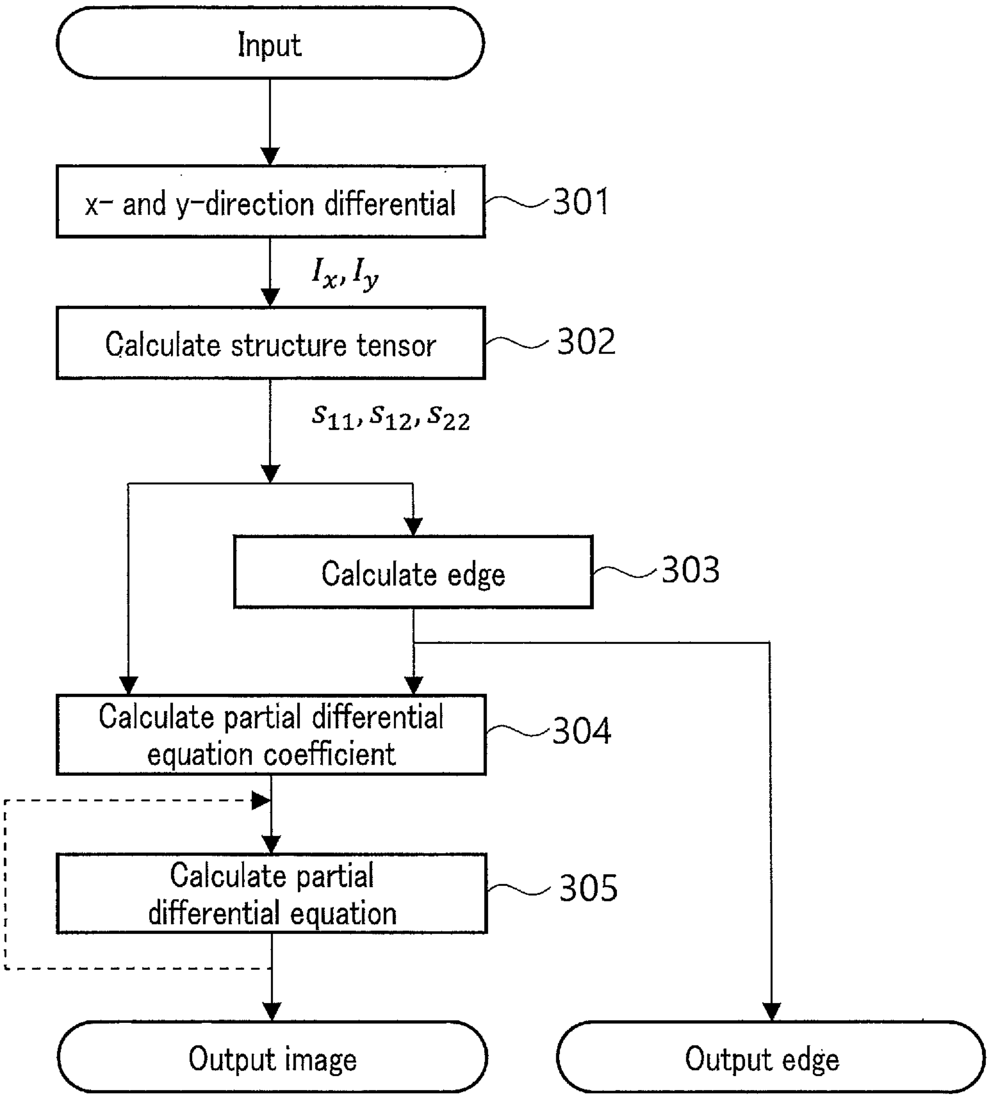
FIG. 3 is a diagram showing a typical flow of a nonlinear anisotropic diffusion filter by the image processing circuitry according to the first embodiment.

FIG. 3 is a diagram showing a typical flow of the nonlinear anisotropic diffusion filter processes 213, 223, and 233 performed by the image processing circuitry 15. The process in step 301 through step 305 is performed for each pixel that constitutes a low-pass image targeted for the process.

As shown in FIG. 3, the image processing circuitry 15 calculates the differential value $I_x$ with respect to the x direction and the differential value $I_y$ with respect to the y direction of a pixel value of a target pixel in a low-pass image (step 301). After the differential values $I_x$ and $I_y$ are calculated, the image processing circuitry 15 performs, as shown in the equation (3), convolutional computation on the calculated differential values $I_x$ and $I_y$ and the two-dimensional Gaussian function $G_\rho$ and calculates elements $s_{11}$, $s_{12}$, and $s_{22}$ of the structure tensor S (step 302). The calculation in step S2 includes a calculation of the two-dimensional Gaussian function $G_\rho$.

After the elements $s_{11}$, $s_{12}$, and $s_{22}$ of the structure tensor S are calculated, the image processing circuitry 15 performs a linear algebraic operation on the calculated elements $s_{11}$, $s_{12}$, and $s_{22}$ by the equation (3) to calculate the first unique value $\mu_1$ and the second unique value $\mu_2$ of the two-dimensional structure tensor S, and calculates the edge size E based on the first unique value $\mu_1$ and the second unique value $\mu_2$ by the equation (4) (step 303). The edge size E is used in the high-pass level control processes 212, 222, and 232. By the equation (3), the rotation matrix R of the two-dimensional structure tensor S, i.e., the edge direction, is calculated.

The image processing circuitry 15 calculates each coefficient used in a numerical analysis of the partial differential equation of the nonlinear anisotropic diffusion filter, based on the elements $s_{11}$, $s_{12}$, and $s_{22}$ of the structure tensor S (step 304). For example, the image processing circuitry 15 calculates the coefficients $c_1$ and $c_2$ by the equations (5) and (6), and calculates each element value $d_{11}$, $d_{12}$, and $d_{22}$ of the diffusion tensor D by the equation (2) based on the coefficients $c_1$ and $c_2$ and the rotation matrix R. The edge size E may be used in the calculation to enhance efficiency of the process. Thereafter, the image processing circuitry 15 performs a numerical analysis calculation of the partial differential equation (step 305). Specifically, the image processing circuitry 15 performs numerical analysis computation on the partial differential equation (1) based on the element values $d_{11}$, $d_{12}$, and $d_{22}$ and the differential values $I_x$ and $I_y$ to calculate an output pixel value. At time t, a new pixel value of a target pixel at time t+Δt is calculated based on pixel values of the target pixel and voxels in the vicinity thereof and each element value of the diffusion tensor, and subsequently the same calculation is repeated once to a few times, using t+Δt as a new t. The calculated pixel value is used in the multiresolution reconstruction processes 214, 224, and 234.

After step 305, steps 301 to 305 are repeated for a different target pixel. After steps 301 to 305 are performed for all pixels constituting a target image, the nonlinear anisotropic diffusion filter processes 213, 223, and 233 by the image processing circuitry 15 are finished.

Returning to FIG. 2, the high-pass level control processes 212, 222, and 232 and the multiresolution reconstruction process 214, 224, 234 will be explained.

In the high-pass level control process 212, 222, or 232 at each level, pixel values of three high-pass images generated by the multiresolution decomposition process 211, 221, or 231 at respectively corresponding levels are controlled by the edge information from the nonlinear anisotropic diffusion filter process 213, 223, or 233 at respectively corresponding levels. The edge information is the size of an edge standardized based on a unique value of a structure tensor. In each of the high-pass level control processes 212, 222, and 232, an integrated value of edge information and each high-pass image is calculated for each pixel, and a control coefficient of each high-pass image is multiplied with the calculated value. As another example of pixel values controlling, a threshold value may be set for the edge size and when an edge size is equal to or greater than the threshold value, the pixel may be considered to be an edge, and a control coefficient of each high pass image may be multiplied with a region other than the edge. Three high-pass images processed in the above-described manner are used in the corresponding multiresolution reconstruction process 214, 224, or 234.

The multiresolution reconstruction process 214, 223, or 234 in each level generates a single synthesized image based on a single low-pass image from the nonlinear anisotropic diffusion filter process 213, 223, or 233 at the same level and three high-pass images from the high-pass level control process 212, 222, or 232 at the same level. The length and width of the synthesized image are twice those of the used low-pass and high-pass images.

The synthesized image that is output by the multiresolution reconstruction process 234 at level 3 is input to the nonlinear anisotropic diffusion filter process 223 at level 2 and subjected to filtering similarly to the level-3 processing, then input to the multiresolution reconstruction process 224 as a low-pass image. On the other hand, the high-pass image that is output from the multiresolution decomposition process 221 at level 2 is subjected to a high-pass level control similarly to the level-3 processing in the high-pass level control processing 222 at level 2 and is input to the multiresolution reconstruction process 224 at level 2 as a high-pass image. The multiresolution reconstruction process 224 at level 2 generates a single synthesized image from a single low-pass image and three high-pass images, in a manner similar to the processing at level 3.

The processing at level 1 is performed in a manner similar to the processing at level 2. In other words, a final synthesized image, namely a resultant image, is obtained by the nonlinear anisotropic diffusion filter process 213, the high-pass level control process 212, and the multiresolution reconstruction process 214 at level 1.

The explanation of the nonlinear image filter applied by the image processing function 152 of the image processing circuitry 15 is finished.

As described above, the nonlinear anisotropic diffusion filter has a few parameters for controlling a strength of a filter and an extent of edge detection, which are both dependent on the direction of a tissue boundary, and the number of such parameters tends to be large as the parameters are prepared for each layer of a multiresolution decomposition. Although a large number of parameters allows an image quality architect to fine-tune an image quality of a filter, it is difficult to quickly reach a desired image quality unless the image quality architect is adept at manipulating the filter.

However, by way of exception, it is possible to adjust the strength of the filter in the entire image by changing a synthesizing ratio of an image before the processing to an image after the processing, thereby providing an operating person with a means for adjusting a filter strength. It is impossible, however, to change the filter in greater detail, for example, to change a filter length only in a tissue boundary portion.

The nonlinear anisotropic diffusion filter is a process of solving a partial differential equation in a manner of numeric analysis and therefore requires an iterative operation in order to obtain a high image quality result with strong filtering; on the other hand, a large number of iterations would require a sufficiently long time for the operation.

The image processing circuitry 15 according to the present embodiment reduces the number of parameters for adjusting image quality (hereinafter "image quality adjustment parameters") to a smaller number compared to that in the nonlinear image filter, and it is thereby possible to minutely adjust desired characteristics among image characteristics proccessable by the nonlinear image filter and to obtain, in turn, a desired image quality simply and quickly. Hereinafter, this process will be called a "simplified image filter". The image quality adjustment parameter is an example of a coefficient value applied to a derived image.

Figure 4:
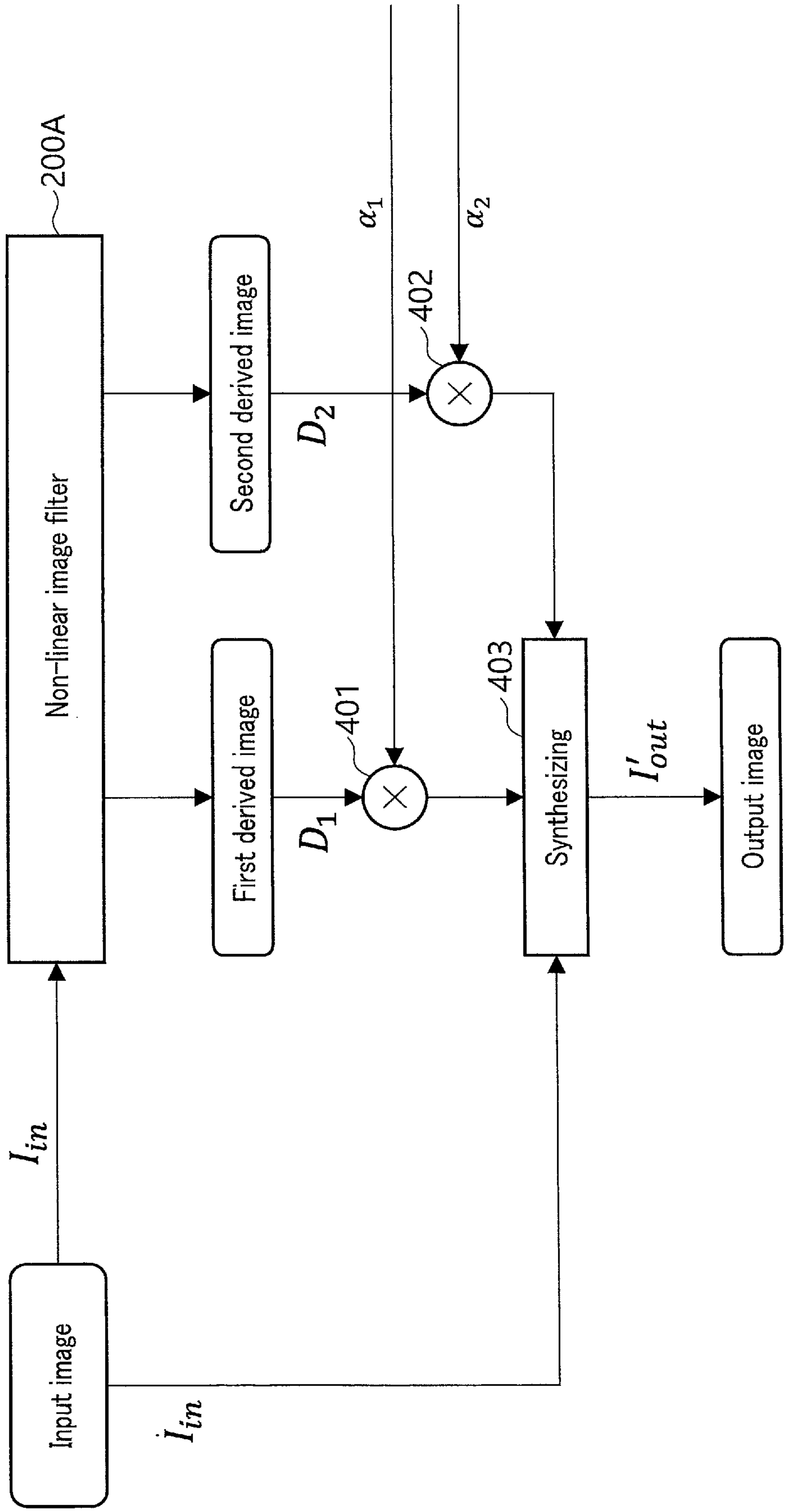
FIG. 4 is a schematic view showing a simplified image filter by the image processing circuitry according to the first embodiment.

FIG. 4 is a schematic view showing a simplified image filter by the image processing circuitry 15. As shown in FIG. 4, the image processing circuitry 15, through the realization of the image processing function 152, applies a nonlinear image filter 200A as the above-described nonlinear image filter. The nonlinear image filter 200A has basically the same processing procedures as those of the nonlinear image filter 200 shown in FIG. 2, except for a calculation for obtaining a first derived image $D_1$ and a second derived image $D_2$. The first derived image $D_1$ and the second derived image $D_2$ are images representing two or more image characteristics to be processed through an application of the nonlinear image filter 200 to an input image $I_{in}$, and they are generated based on a first output image $I_{out}$ generated by applying the nonlinear image filter 200 to the input image $I_{in}$, a second output image generated by applying the nonlinear image filter 200A to the input image $I_{in}$ when a parameter used for the nonlinear image filter 200A is set to a predetermined value, and the input image $I_{in}$. The parameter differs from an image quality adjustment parameter, and is a parameter normally used in the nonlinear image filter 200A. Hereinafter, the parameter will be called a "filter parameter".

Herein, the input mage $I_{in}$ is a B-mode image that is input to the nonlinear image filter 200A. Two or more image characteristics to be processed through an application of the nonlinear image filter 200 are, for example, smoothing of a tissue boundary (a tissue boundary in an edge direction) or a substantial part of tissue, emphasizing of a tissue boundary (a tissue boundary in a direction orthogonal to an edge), or reduction in (or smoothing of) speckles. The filter parameter may be any of the following: an edge size, an edge direction, elements $s_{11}$, $s_{12}$, and $s_{22}$ of a structure tensor S, differential values $I_x$ and $I_y$, unique values $\mu_1$ and $\mu_2$, a parameter k, or any kind of parameter used with the nonlinear image filter 200, for example.

A procedure of generating a first derived image $D_1$ and a second derived image $D_2$ will be specifically explained. The image processing circuitry 15 applies the nonlinear image filter 200A to an ultrasound image (B-mode image) to generate a resultant image, namely a normal output image $I_{out}$. The edge size E when a normal output image $I_{out}$ is generated is generated at step 303 shown in FIG. 3. The image processing circuitry 15 generates, before acquiring each derived mage, an output image $I_0$ when the edge size E is set to 0, apart from the normal output image $I_{out}$. Specifically, the image processing circuitry 15 calculates a first unique value and a second unique value when edge size E=0 shown in the equation (4), and calculates coefficients $c_1$ and $c_2$ in accordance with the equations (5) and (6). The image processing circuitry 15 then calculates the partial differential equation following the equation (1) based on the first unique value $\mu_1$, the second unique value $\mu_2$, and coefficients $c_1$ and $c_2$, and generates an output image $I_0$. Regarding the edge size, the edge size used by the nonlinear anisotropic image filter 213, 223, 233 at all levels may be set to zero, but it suffices for the edge size used by the nonlinear anisotropic image filter 213 at at least level 1 to be set to zero. The output image $I_0$ corresponds to a resultant image in which smoothing is applied without a consideration of a tissue boundary.

The image processing circuitry 15 generates a first derived image $D_1$ as a subtraction image obtained from the output image $I_0$ and an input image $I_{in}$ based on the equation (7) shown below, and generates a second derived image $D_2$ as a subtraction image obtained from the output image $I_{out}$ and the output image $I_0$ based on the equation (7). The first derived image $D_1$ is a subtraction image of the output image $I_0$ and the input image $I_{in}$ and includes image components for smoothing. In other words, the first derived image $D_1$ is an image that represents smoothing of a tissue structure, etc. included in an ultrasound image, which is an image characteristic processed by the nonlinear image filter 200A. The second derived image $D_2$ is a subtraction image of the output image $I_{out}$ and the output image $I_0$ and includes image components for emphasizing of a tissue boundary. In other words, the second derived image $D_2$ is an image that represents emphasizing of a boundary of tissue structures included in an ultrasound image, which is an image characteristic processed by the nonlinear image filter 200A.

$$D_1 = I_0 - I_{in} \tag{7}$$

$$D_2 = I_{out} - I_0 \tag{8}$$

From the equations (7) and (8), the output image $I_{out}$ in a case where no adjustment is made can be expressed by the equation (9) as follows:

$$I_{out} = I_{in} + D_1 + D_2 \tag{9}$$

When the nonlinear image filter 200A is performed, the image processing circuitry 15 performs, through a realization of the adjustment function 153, the first adjustment process 401 and the second adjustment process 402. In the first adjustment process 401, the image processing circuitry 15 multiplies the image adjustment parameter $\alpha_1$ with the first derived image $D_1$, thereby generating an adjusted first derived image $\alpha_1 D_1$. In the second adjustment process 402, the image processing circuitry 15 multiplies the image adjustment parameter $\alpha_2$ with the second derived image $D_2$, thereby generating an adjusted second derived image $\alpha_2 D_2$. The image quality adjustment parameters $\alpha_1$ and $\alpha_2$ are a real number in the range from 0 to 1. The image quality adjustment parameters $\alpha_1$ and $\alpha_2$ are adjustable independently from each other. A strength of an image component for emphasizing of a tissue boundary included in the first derived image $D_1$ can be adjusted through adjustment of the image quality adjustment parameter $\alpha_1$, and a strength of an image component for smoothing included in the second derived image $D_2$ can be adjusted through adjustment of the image quality adjustment parameter $\alpha_2$. The image quality adjustment parameters $\alpha_1$ and $\alpha_2$ are separately adjustable by an operating person via the input device 19, etc.

When the first adjustment process 401 and the second adjustment process 402 are performed, the image processing circuitry 15 performs the synthesizing function 154. With the synthesizing function 154, the image processing circuitry 15 combines the input image $I_{in}$, the adjusted first derived image $\alpha_1 D_1$, and the adjusted second derived image $\alpha_2 D_2$, thereby generating a synthesized image $I'_{out}$. As a synthesizing method, for example, the image processing circuitry 15 follows the equation (10) shown below and adds an input image $I_{in}$, the adjusted first derived image $\alpha_1 D_1$, and the adjusted second derived image $\alpha_2 D_2$, thereby generating a synthesized image $I'_{out}$.

$$I'_{out} = I_{in} + \alpha_1 D_1 + \alpha_2 D_2 \tag{10}$$

The synthesizing method is not limited to a summation and can be achieved through various methods, such as multiplication or inverted multiplication, etc.

After the synthesized image $I'_{out}$ is generated, the simplification image filter by the image processing circuitry 15 is completed. Thereafter, the image processing circuitry 15 performs the display control function 155 to cause the display device 16 to display the synthesized image $I'_{out}$. At this time, the image processing circuitry 15 may arrange not only the synthesized image $I'_{out}$ but the input image $I_{in}$ and/or the first output image $I_{out}$ side by side, so that these images are displayed superposed or displayed in a manner where one can be switched to another.

The simplified image filter is thus finished. It should be noted that the above simplified image filter is merely an example, and the present embodiment is not limited thereto. For example, the derived images in the above processing are a subtraction image of two different nonlinear image processes; however, the images are not limited to this example as long as the image may be an image in which a sum of pixel values or numerical analysis values in a spatially global image range becomes approximately zero. As the numeric analysis value, for example, a differential value of a pixel value is adopted. In connection with this, the derived images may be a summation image and a multiplication image, etc. created in a nonlinear image process.

In the above-described process example, the first derived image is a subtraction image of an output image $I_0$ of the nonlinear image filter and an input image $I_{in}$ when the edge size is set to zero; however, it may be a subtraction image of an output image $I_0$ of the nonlinear image filter and an input image $I_{in}$ when the edge size is set to a discretional value, for example 1. Furthermore, it suffices that the derived images are an image that represents image characteristics to be processed by a nonlinear image filter; in other words, it suffices that the output image $I_0$ is an output image of a nonlinear image filter when a discretionarily selected filter parameter other than the edge size is set to a discretional value. Selecting a type and a setting value of a filter parameter as appropriate makes it possible to generate a derived image as appropriate that represents discretionarily chosen image characteristics processed by a nonlinear image filter.

For example, the image characteristics of a derived image in the foregoing example processing is dependent on edge information calculated by following the equation (4); however, the image characteristics may be dependent on a spatial differential of an image or a difference between pixel values.

In the foregoing example processing, the nonlinear image filter 200A includes a nonlinear anisotropic diffusions filter as a constituent element; however, it may include various image filters other than a nonlinear anisotropic diffusion filter and it may include more than one image filter.

The nonlinear image filter 200A, which is an example of a nonlinear image filter, is a process of applying a nonlinear anisotropic diffusion filter at each level of multiresolution analysis, as shown in FIG. 2. For example, as shown in the equations (4) to (6), etc., the nonlinear anisotropic diffusion filter itself has many filter parameters for image quality adjustment; furthermore, there are as many filter parameter groups as the number of levels of multiresolution analysis. If things continue in this manner, it will be difficult to reach a desired image quality.

As described above, according to the present embodiment, multiple filter parameters used with the linear image filter, such as an anisotropic diffusion filter, are not adjusted; rather, two or more image quality adjustment parameters respectively corresponding to two or more images derived from the nonlinear anisotropic diffusion filter are adjusted. A derived image is an image in which various image components to be emphasized or reduced by the nonlinear image filter are contracted; therefore, an image quality adjustment parameter corresponding to a derived image is a parameter with which an image component represented by the derived image is adjusted. For example, since the first derived image $D_1$ represents image components for smoothing, the image quality adjustment parameter $\alpha_1$ mainly functions as a parameter for adjusting a smoothing strength; similarly, since the second derived image $D_2$ represents image components for emphasis, the image quality adjustment parameter $\alpha_1$ mainly functions as a parameter for adjusting a strength of tissue boundary emphasis. The image quality adjustment parameter $\alpha_1$ and $\alpha_2$ can be considered to be significant parameters. According to the present embodiment, an operating person only needs to adjust an image quality parameter directly related to a particular image component; thus, this allows the person to adjust image quality intuitively and easily. Furthermore, since there are a small number of image quality adjustment parameters, it is possible to reach a desired image quality easily.

Various application examples of the first embodiment will be explained below.

Application Example 1

In the foregoing embodiment, the image quality adjustment parameters $\alpha_1$ and $\alpha_2$ can be set by an operating person via the input device 19. The image quality adjustment parameters $\alpha_1$ and $\alpha_2$ are set via a GUI screen (hereinafter called a "parameter setting screen"). The parameter setting screen is generated by the display control function 155 of the image processing circuitry 15 and displayed on the display device 16. The parameter setting screen is displayed on the input device 19 in an operable manner. The parameter setting screen may be displayed on a touch panel in which the display device 16 is integrated into the input device 19 or on a display device 16 such as a display etc. physically separate from the input device 19.

Figure 5:
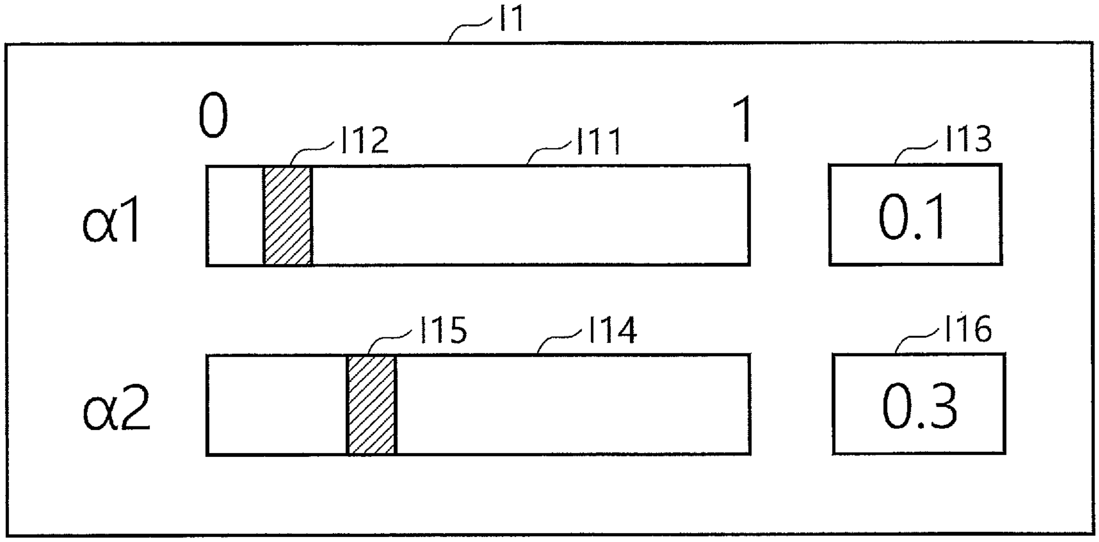
FIG. 5 is a diagram showing an example of a parameter setting screen according to Application Example 1.

FIG. 5 is a diagram showing an example of the parameter setting screen I1 according to Application Example 1. As shown in FIG. 5, a slider bar I11 for setting the image quality adjustment parameter $\alpha_1$ is displayed on the parameter setting screen I1. The image quality adjustment parameter $\alpha_1$ is assigned to the slider bar I11, and a lower limit value (for example "0") to an upper limit value (for example "1") of the image quality adjustment parameter $\alpha_1$ are sequentially assigned from the left to the right of the bar, for example. A tab I12 is provided on the slider bar I11. The tab I12 is provided in such a manner that it can freely move along the slider bar I11. By arranging, via the input device 19, the tab I12 at a discretional position on the slider bar I11, the image quality adjustment parameter $\alpha_1$ is set to a value corresponding to the discretional position. The setting value of the image quality adjustment parameter $\alpha_1$ is displayed on the display section I13. In the example of FIG. 5, the setting value of the image quality adjustment parameter $\alpha_1$ is set to "0.1" as shown. Similarly for the image quality adjustment parameter $\alpha_2$, the slider bar I14 to which values ranging from a lower limit value to an upper limit value of the image quality adjustment parameter $\alpha_2$ are assigned, the tab I15 for setting the image quality adjustment parameter $\alpha_2$, and the display section I16 indicating a set value ("0.3" in the example of FIG. 5) of the image quality adjustment parameter $\alpha_2$ are displayed.

Figure 6:
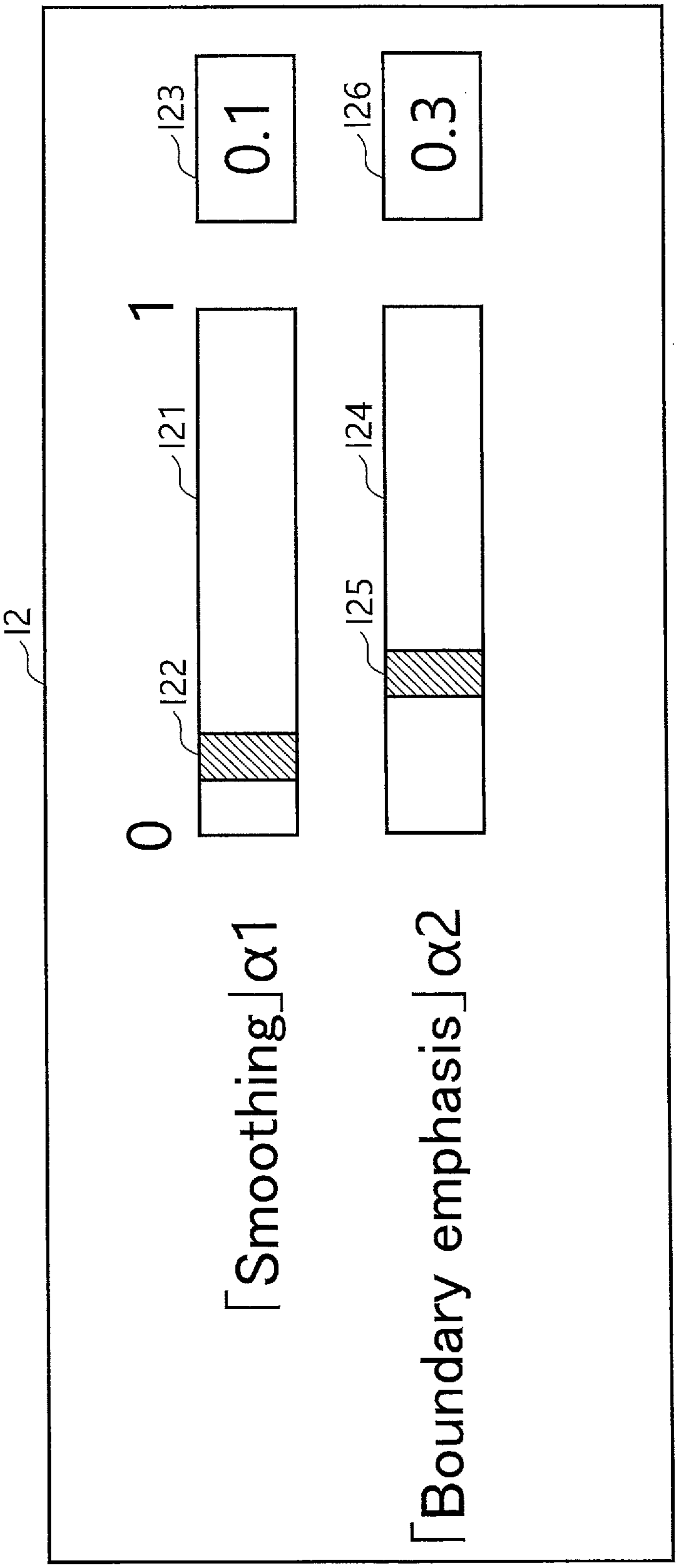
FIG. 6 is a diagram showing an example of another parameter setting screen according to Application Example 1.

FIG. 6 is a diagram showing an example of another parameter setting screen I2 according to Application Example 1. As shown in FIG. 6, the slider bar I21 to which values from a lower limit value to an upper limit value of the image quality adjustment parameter $\alpha_1$ is assigned, the tab I22 with which the image quality adjustment parameter α1 is set, and a display section I23 indicating the set value of the image quality adjustment parameter $\alpha_1$, are displayed. The slider bar I21, the tab I22, and the display section I23 are the same as the slider bar I11, the tab I12, and the display section I13 shown in FIG. 5. In the parameter setting screen I2, as an explanation of the image adjustment parameter $\alpha_1$, for example a caption "smoothing" is displayed for the slider bar I21, the tab I22, and the display section I23. Similarly, as an explanation of the image quality adjustment parameter α2, for example a caption "tissue boundary emphasis" is displayed for the slider bar I24, the tab I25, and the display section I26.

The explanation of the image quality adjustment parameter targeted for setting is not limited to a text; a pictogram or the like may be displayed as a caption.

As described above, in the parameter setting screens I1 and I2, input components (GUI components), such as a slider bar and a tab, etc., for inputting a setting value for each image quality adjustment parameter are provided.

Figure 7:
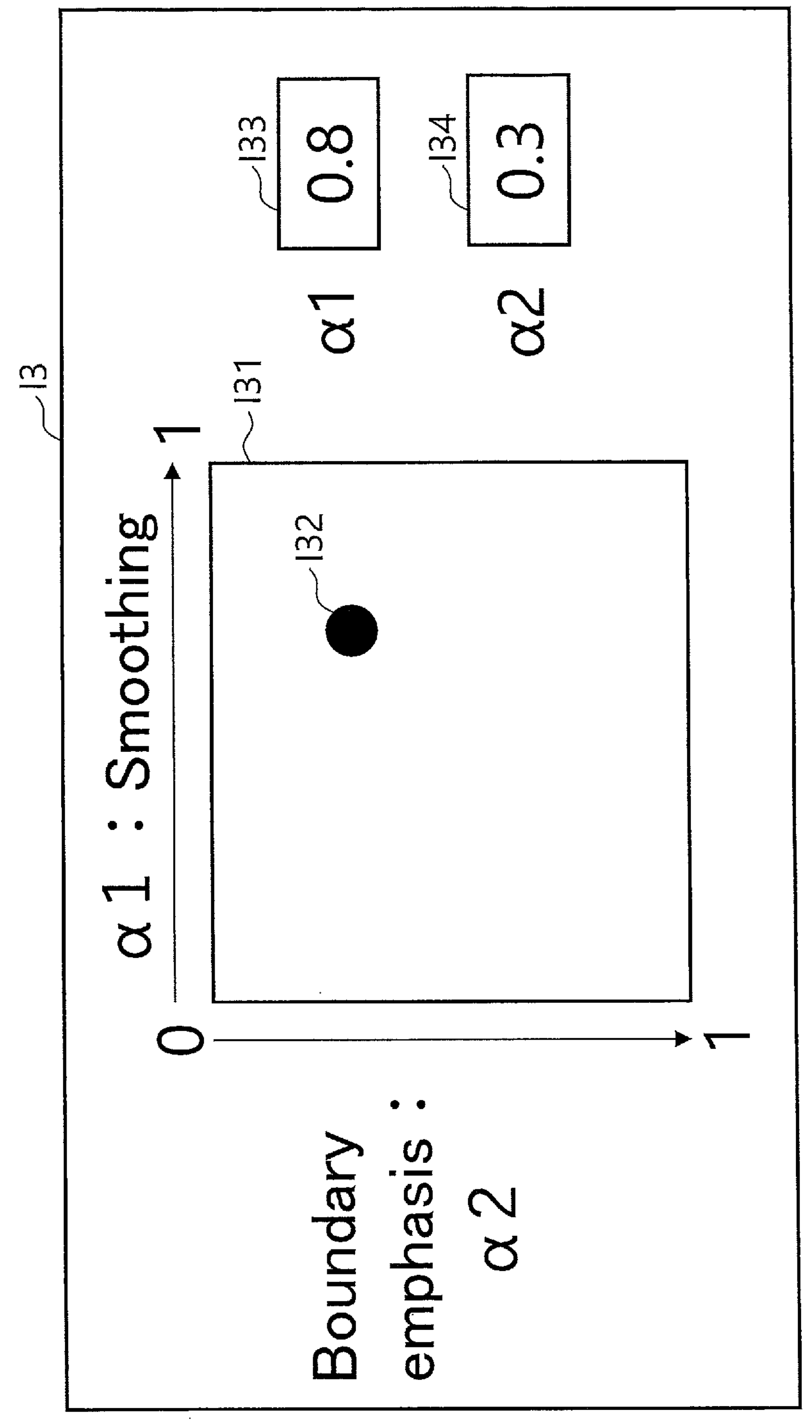
FIG. 7 is a diagram showing an example of another parameter setting screen according to Application Example 1.

FIG. 7 is a diagram showing an example of another parameter setting screen I3 according to Application Example 1. As shown in FIG. 7, the parameter setting screen I3 displays an input component (GUI component) I31 for setting values of both of the image quality adjustment parameter $\alpha_1$ and $\alpha_2$ with a single operation. The input component I31 is hereinafter called a "setting field". The setting field I31 is a GUI component having a coordinate space of a number of dimensions corresponding to the number of image quality adjustment parameters. In the present embodiment, the number of image quality adjustment parameters is "2"; therefore, the setting field I31 is a two-dimensional coordinate space. Specifically, in the setting field I31, the horizontal axis indicates the image quality adjustment parameter $\alpha_1$ and the vertical axis indicates the image quality adjustment parameter $\alpha_2$, and a combination of the image quality adjustment parameter $\alpha_1$ and $\alpha_2$ is assigned to each coordinate. In the horizontal axis, values from a lower limit value (for example "0") to an upper limit value (for example "1") are sequentially assigned from the left to the right of the axis; in the vertical axis, values from a lower limit value (for example "0") to an upper limit value (for example "1") are sequentially assigned from the top to the bottom of the axis. In the setting field I31, the tab I32 is provided in a freely movable manner. By arranging, via the input device 19, the tab I32 at a discretional position on the slider bar I31, the image quality adjustment parameters $\alpha_1$ and $\alpha_2$ are set to values corresponding to the discretional position. The setting value of the image quality adjustment parameter $\alpha_1$ ("0.8" in the example of FIG. 7) is displayed in the display section I33, and the setting value of the image quality adjustment parameter $\alpha_2$ ("0.3" in the example of FIG. 7) is displayed in the display section I34.

As described above, according to Application Example 1, the image quality adjustment parameters can be set using the GUI screen. Through using the GUI screen, an operating person can set the image quality adjustment parameters intuitively and easily.

In Application Example 1, the parameter setting screens I1, I2, I3 and the GUI components I11-I16, I21-I26, I31-I34 may be mechanical components provided in the input device 19. These mechanical components may be implemented by an operation panel provided in the apparatus main body of the ultrasonic diagnostic system 1, for example.

Application Example 2

The above embodiment assumed that the image quality adjustment parameters have a constant value for all pixels constituting a derived image. Since ultrasonic waves tend to be greatly affected by attenuation and experience frequency-dependent attenuation, image quality greatly differs between a shallow portion and a deep portion in an ultrasound image. Furthermore, with a certain type of ultrasonic probe 11, an ultrasound image is generated in a shape of a fan, and a deep portion of such a fan-shaped image tends to have a coarse scanning density and therefore to have a coarse image quality; therefore, there are differences in how the image processing affects a shallow portion and a deep portion. For this reason, the image processing under the setting suitable for a shallow portion strongly applies to a deep portion on one hand; on the other hand, the image processing under the setting suitable for a deep portion only weakly applies to a shallow portion. Thus, even when the image quality adjustment parameters are set to a constant value for the entire image, the effect of the nonlinear image filter, such as the nonlinear anisotropic diffusion filter, cannot be obtained uniformly from the entire image.

Suppose the image quality parameters according to Application Example 2 have values according to a spatial position in a derived image. The image processing circuitry 15 according to Application Example 2, with realization of the adjustment function 153, sets a value of an image quality adjustment parameter in accordance with a spatial position of a derived image. For example, for each of the image adjustment parameters $\alpha_1$ and $\alpha_2$, the image processing circuitry 15 stores functions defining an adjustment rate of the image adjustment parameter which is dependent on a spatial position in a derived image. It suffices that the adjustment rate is defined as an amount of deviation from a reference value of the image quality adjustment parameter or a ratio of the image quality adjustment parameter to a reference rate. It suffices that a reference value is set via the parameter setting screen shown in FIGS. 5 to 7 of Application Example 1.

Figure 8:
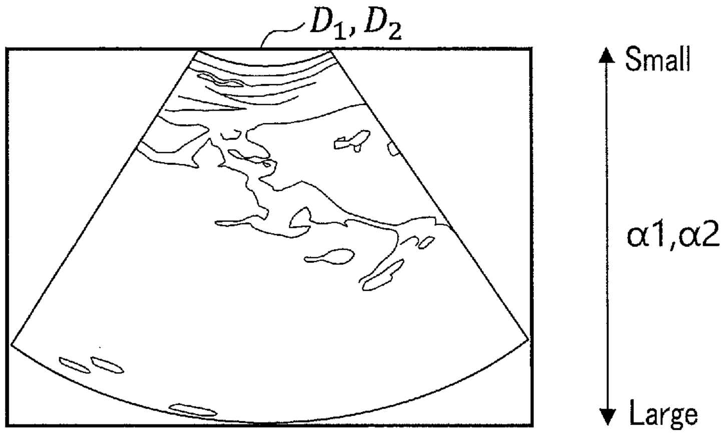
FIG. 8 is a schematic diagram showing transition of set values of image quality adjustment parameters $\alpha_1$ and $\alpha_2$ in accordance with a depth location.

The adjustment rate is used to correct frequency dependent attenuation between different spatial positions and a difference in scanning line intensity between different spatial positions. The influence of the frequency dependent attenuation and scanning line intensity appear more strongly in the acoustic line direction (depth direction) of an ultrasonic wave than in the acoustic scanning direction; therefore, as shown in FIG. 8, the image quality adjustment parameters $\alpha_1$ and $\alpha_2$ may be set in such a manner that they are dependent only on the depth position. For example, it suffices that the image quality adjustment parameter $\alpha_1$ and $\alpha_2$ for a pixel at a deeper position are set to larger values.

With respect to a pixel value of each pixel in the first derived image $D_1$, the image processing circuitry 15 specifies a spatial position of the pixel, and calculates an adjustment rate of the image quality adjustment parameter $\alpha_1$ of the pixel by applying the pixel value and the spatial position of the pixel to the function. The image processing circuitry 15 multiplies the calculated adjustment rate with a reference value to calculate a value of the image quality adjustment parameter $\alpha_1$ of the pixel, and applies the calculated value of the image quality adjustment parameter $\alpha_1$ to the pixel value of the pixel to calculate an adjusted pixel value. It is possible to generate an adjusted first derived image by performing the same operation on all pixels of the first derived image $D_1$. The same applies to the second derived image $D_2$. The adjustment rate may be set to different values or the same value for the image quality adjustment parameter $\alpha_1$ and the image quality adjustment parameter $\alpha_2$.

The image processing circuitry 15 may store, instead of functions, a lookup table (LUT) in which a spatial position is associated with an adjustment rate of the image quality adjustment parameter. In this case, it suffices that the image processing circuitry 15 specifies the adjustment rate of the image quality adjustment parameter by applying the LUT to each pixel of a derived image, calculates a value of the image quality adjustment parameter of the pixel by multiplying the specified adjustment rate with the reference value, and applies the calculated value of the image quality adjustment parameter to the pixel value of the pixel, thereby obtaining an adjusted pixel value.

According to Application Example 2, the value of the image quality adjustment parameter can be changed in accordance with a spatial position in the derived image. It is thereby possible to obtain effects of a nonlinear image filter, such as a nonlinear anisotropic diffusion filter, uniformly in the entire image.

Application Example 3

In the foregoing embodiment, there are two derived images and therefore there are two image quality adjustment parameters. In Application Example 3, suppose the number of derived images and the number of image quality adjustment parameter types are "n" for the sake of generalization. Herein, "n" is an integer equal to or greater than 2.

Figure 9:
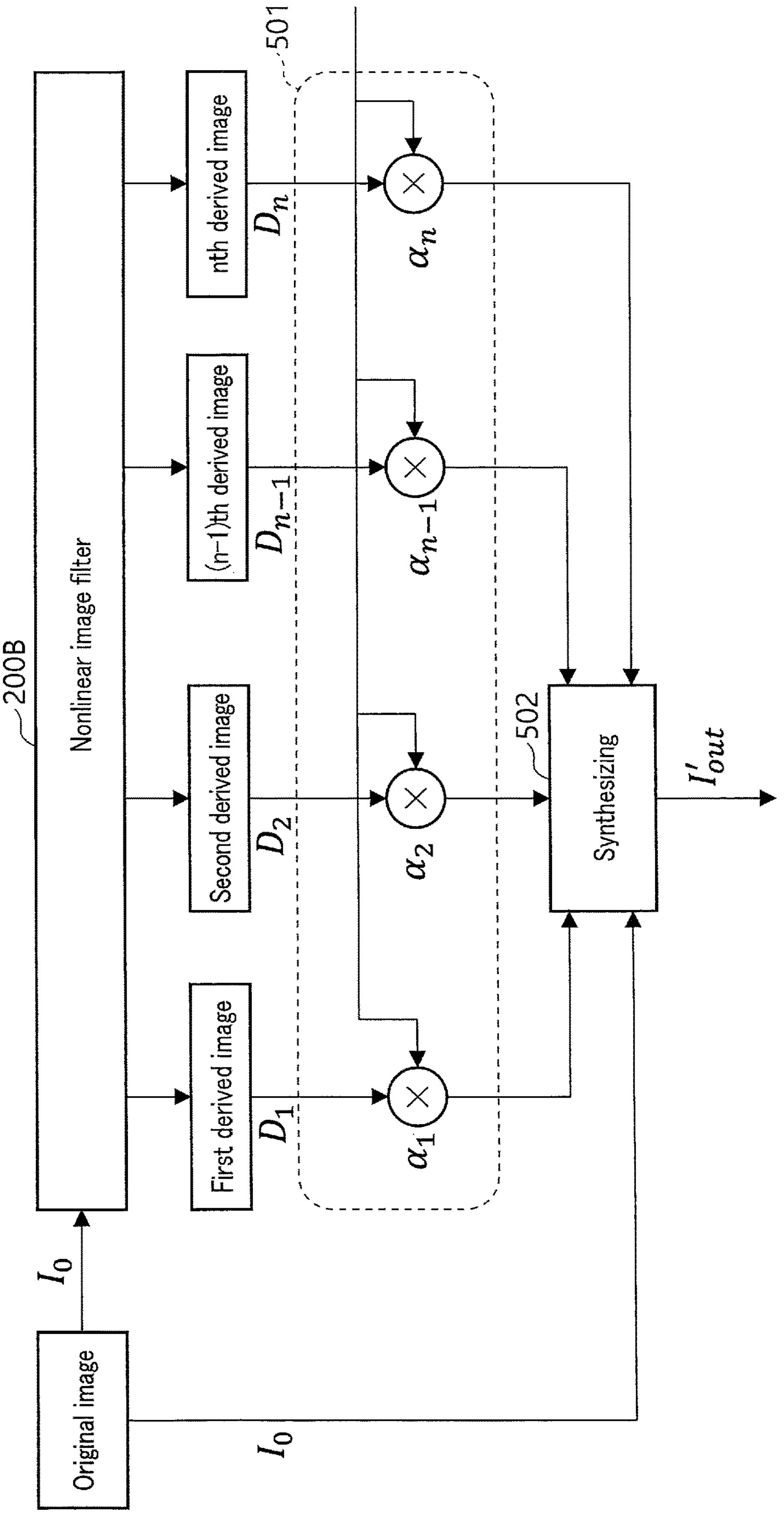
FIG. 9 is a schematic diagram showing a simplified image filter according to Application Example 3.

FIG. 9 is a schematic diagram showing a simplified image filter according to Application Example 3. As shown in FIG. 9, the image processing circuitry 15, through the realization of the image processing function 152, applies a nonlinear image filter 200B as the nonlinear image filter. The nonlinear image filter 200B is the same as the nonlinear image filter 200A shown in FIG. 4, except that the number of derived images generated by the filter is "n" in the former.

When the nonlinear image filter 200B is applied, the image processing circuitry 15 performs, through a realization of the adjustment function 153, an adjustment process 501. In the adjustment process 501, the image processing circuitry 15 multiplies the image adjustment parameter $\alpha_k$ with the $k^{th}$ derived image $D_k$ (k is an index of the derived image; $1 \le k \le n$), thereby generating an adjusted $k^{th}$ derived image $\alpha_k D_k$. The image quality adjustment parameter $\alpha_k$ is a real number in the range from 0 to 1. The image quality adjustment parameters $\alpha_k$ are adjustable independently from each other. The image quality adjustment parameters $\alpha_k$ are separately adjustable by an operator via the input device 19, etc. For example, an output image $I_0$ when the edge size is set to "0" and an output image $I_1$ when the edge size is set to "1" are calculated so that it is possible to generate a first derived image based on an input image $I_{in}$ and an output image $I_0$, a second derived image based on an output image $I_0$ and an output image $I_{out}$, a third derived image based on an input image $I_{in}$ and an output image $I_1$, and a fourth derived image based on an output image $I_1$ and an output image $I_{out}$. It is also possible to generate a derived image based on an output image when the other filter parameters are set to zero or a predetermined value and an input image $I_{in}$, or to generate a derived image based on an output image when the other filter parameters are set to zero or a predetermined value and an output image $I_{out}$.

After the adjustment process 501, the image processing circuitry 15 performs a synthesizing process 502 through realization of the synthesizing function 154. In the synthesizing processing 502, the image processing circuitry 15 synthesizes the input image $I_{in}$, the adjusted first derived image $\alpha_1 D_1$, and the adjusted second derived image $\alpha_2 D_2$, thereby generating a synthesized image $I'_{out}$. As a synthesizing method, for example, the image processing circuitry 15 follows the equation (11) shown below and adds an input image $I_{in}$ and the adjusted $k^{th}$ derived image $\alpha_k D_k$, thereby generating a synthesized image $I'_{out}$. The synthesized image $I'_{out}$ is displayed on the display device 16.

$$I'_{out} = I_{in} + \sum_{k=1}^{n} (\alpha_k D_k) \tag{11}$$

Similarly to the foregoing application examples, the synthesizing method is not only limited to a summation in Application Example 3; synthesizing can be achieved through various methods, such as multiplication or inverted multiplication, etc.

According to Application Example 3, it is possible to generate a synthesized image $I'_{out}$ based on three or more derived images. It is thus possible to adjust the image quality of a synthesized image $I'_{out}$ in more detail.

Second Embodiment

In the first embodiment, it is necessary to calculate a nonlinear image filter in order to obtain an output image $I_{out}$, which is required to obtain a derived image. Since the calculation of the nonlinear image filter is complicated and requires time, a processing time will be increased if the number of times of repeating the calculation of a nonlinear anisotropic diffusion filter is increased in order to attain strong processing.

As a solution to this problem, an output image for an unknown input image may be inferred using a machine learning model, which is trained by a set of input and output images of a nonlinear image filter, and output as the resultant output image. However, with such a machine learning method, there is no means of adjusting image quality other than adjusting a filter strength on the entire image by changing a synthesizing ratio between images before and after processing.

The ultrasonic diagnostic system 1 according to the second embodiment uses a machine learning model that outputs a derived image. Hereinafter, the ultrasonic diagnostic system 1 according to the second embodiment will be described below. Note that in the following description, the same reference numerals denote constituent elements having almost the same functions as those included in the first embodiment, and a repeat description will be made only when required.

As a machine learning model according to the second embodiment, a neural network having two or more layers is used. Any type of neural network architecture can be adopted as long as an image can be input thereto and an image can be output therefrom; for example, a CNN (convolutional neural network) or a developed CNN may be used.

Figure 10:
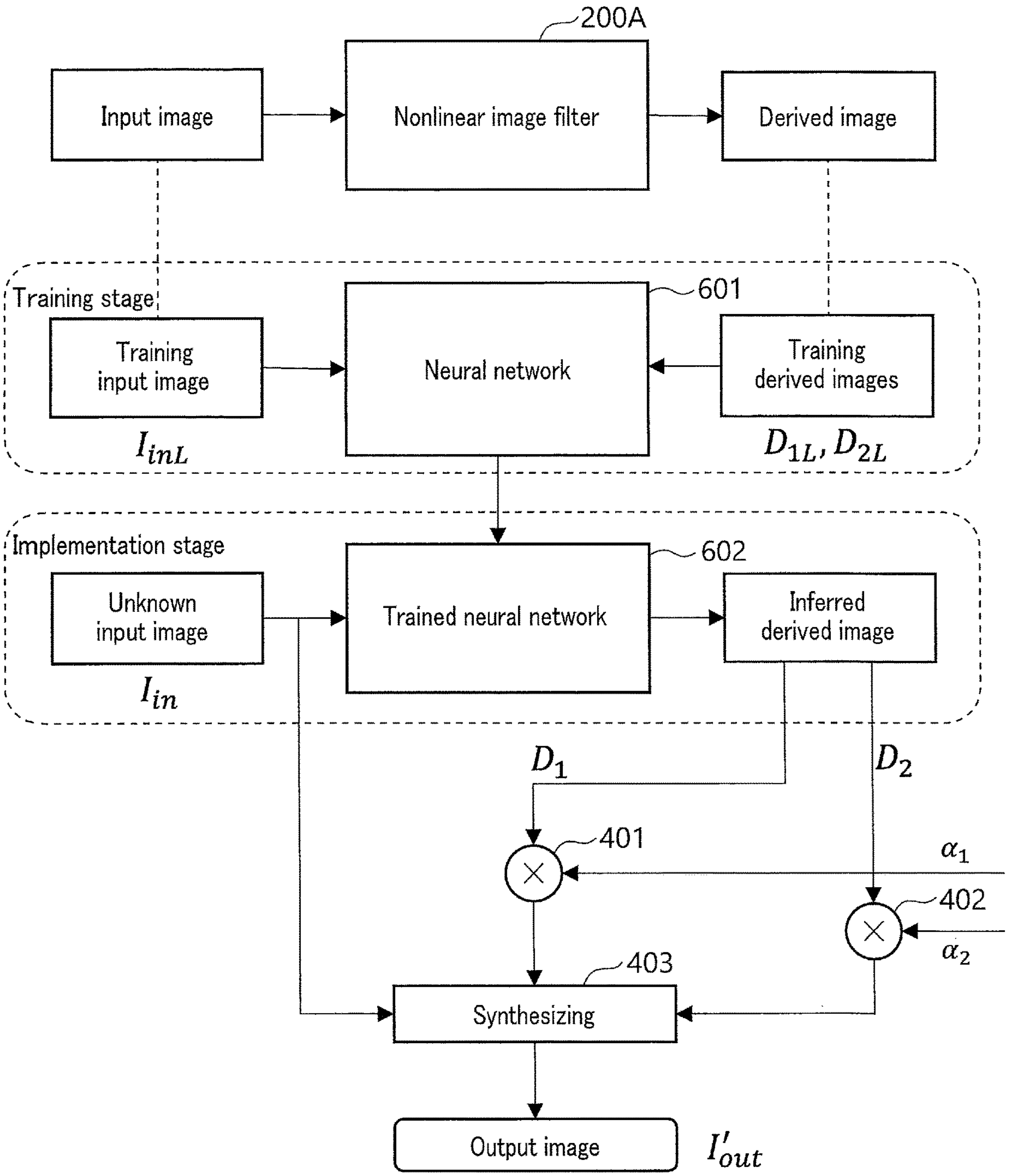
FIG. 10 is a perspective diagram showing a simplified image filter according to a second embodiment.

FIG. 10 is a perspective diagram showing a simplified image filter according to the second embodiment. As shown in FIG. 10, a simplified image filter can be divided into a training stage and an implementation stage. In a training stage, the image processing circuitry 15 is trained with an untrained neural network 601 based on a plurality of training samples and generates a trained neural network 602. A training sample is a set of training input image $I_{inL}$, which is input data, and training derived images $D_{1L}$ and $D_{2L}$, which is training data. The training derived image is a combination of a first derived image $D_{1L}$ and a second derived image $D_{2L}$ according to the first embodiment. The training input image $I_{inL}$ and the training derived image $D_{1L}$ may be input to and output from the neural network 601 in any format; for example, they may be input and output as a multi-dimensional vector having a number of elements corresponding to the number of pixels. Each element has a pixel value of a pixel corresponding to the element as an element value. In this case, it suffices that the output is treated as a multidimensional vector having a number of elements corresponding to the total number of pixels of the training derived images $D_{1L}$ and $D_{2L}$. It suffices that the training derived image $D_{1L}$ and $D_{2L}$ are generated by performing the simplified image filter according to the first embodiment on an arbitrarily selected training input image $I_{inL}$.

The training method is not limited to a particular one. For example, the image processing circuitry 15 determines a learnable parameter of the neural network 601 through supervised training in such a manner that the network outputs a first derived image $D_{1L}$ and a second derived image $D_{2L}$ upon input of a training input image $I_{inL}$. The learnable parameter includes a weight parameter or a bias, etc.

More specifically, the image processing circuitry 15 performs forward propagation processing by applying the neural network 601 of the training input image $I_{in}$ and outputs a first inferred derived image and a second inferred derived image. Next, the image processing circuitry 15 applies, to the neural network 601, a difference (error) between a set of the first inferred derived image and the second inferred derived image and a set of the first derived image $D_{1L}$, and the second derived image $D_{2L}$ and performs backpropagation processing, and thereby calculates a gradient vector, which is a differential coefficient of an error function which is a function of a learnable parameter. Subsequently, the processing circuitry 15 updates the learnable parameters based on the gradient vector. These forward propagation processing, backpropagation processing, and parameter updating processing are repeated with the change of training samples, and a learnable parameter that minimizes an error function is determined in accordance with a predetermined optimization method. A trained neural network 602 is thus generated. The trained neural network 602 is stored in the storage device 17. The trained neural network 602 is implemented in the ultrasonic diagnostic system 1 as a replacement of the nonlinear image filter 200A.

In the implementation stage, the image processing circuitry 15 supplies an unknown input image $I_{in}$ to the trained neural network 602 to infer a derived image column ($D_1$, $D_2$). Thereafter, the image processing circuitry 15 applies, similarly to the first embodiment, the image quality adjustment parameter $\alpha_1$ to the first derived image $D_1$ to generate an adjusted first derived image $\alpha_1 D_1$ by the adjustment process 401, and applies the image quality adjustment parameter α2 to the second derived image D2 to generate an adjusted second derived image $\alpha_1 D_2$ by the adjustment process 402. Then, the image processing circuitry 15 generates a synthesized image $I'_{out}$ by adding the input image $I_{in}$, the adjusted first derived image $\alpha_1 D_1$, and the adjusted second derived image $\alpha_1 D_2$ following the equation (10), for example. The synthesized image $I'_{out}$ is displayed on the display device 16.

The simplified image filter according to the second embodiment is thus finished.

In the foregoing description, the number of derived images is two but can be increased to n, similarly to Application Example 3 of the first embodiment. In this case, it suffices that the nonlinear image filter 200B shown in FIG. 9 is performed in the training stage, instead of the nonlinear image filter 200A shown in FIG. 10. The second embodiment is also combinable with Application Examples 1 to 3 of the first embodiment.

According to the second embodiment, it is possible to obtain a derived image directly from an input image using a trained neural network in the implementation stage, without performing a nonlinear image filter. It is thereby possible to reduce a processing time and calculation loads with a simplified image filter, compared to the first embodiment in which a nonlinear image filter is performed.

According to at least one of the above-described embodiments, it is possible to simplify an adjustment of image quality in the image processing relating to ultrasound diagnosis.

The term "processor" used in the above explanation indicates, for example, a circuit, such as a CPU, a GPU, or an Application Specific Integrated Circuit (ASIC), and a programmable logic device (for example, a Simple Programmable Logic Device (SPLD), a Complex Programmable Logic Device (CPLD), and a Field Programmable Gate Array (FPGA)). The processor realizes its function by reading and executing the program stored in the storage circuitry. The program may be directly incorporated into the circuit of the processor instead of being stored in the storage circuit. In this case, the processor implements the function by reading and executing the program incorporated into the circuit. The function corresponding to the program may be realized by a combination of logic circuits, not by executing the program. Each processor of the present embodiment is not limited to a case where each processor is configured as a single circuit; a plurality of independent circuits may be combined into one processor to realize the function of the processor. In addition, a plurality of structural elements in FIG. 1 may be integrated into one processor to realize the function.

While certain embodiments have been described, these embodiments have been presented by way of example only, and are not intended to limit the scope of the inventions. Indeed, the embodiments described herein may be embodied in a variety of other forms; furthermore, various omissions, substitutions, changes, and combinations of embodiments in the form of the embodiment described herein may be made without departing from the spirit of the invention. The accompanying claims and their equivalents are intended to cover such forms or modifications as would fall within the scope and spirit of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An ultrasonic diagnostic system comprising:

processing circuitry configured to:

generate first and second derived images by applying a trained model to a target ultrasound image on a subject, the first derived image comprising a first image component for smoothing, the second derived image comprising a second image component for emphasizing a tissue structure, the trained model being a neural network trained to output, in response to input of an ultrasound image, an image comprising an image component for smoothing and an image comprising an image component for emphasizing a tissue structure;

input a variable first adjustment parameter value and a second adjustment parameter value corresponding to respective of the first and second derived images;

generate first and second adjusted derived images, the first adjusted derived image being generated by applying the variable first adjustment parameter value for adjusting a smoothing strength to the first derived image, the second adjusted derived image being generated by applying the second adjustment parameter value for adjusting a strength of tissue boundary emphasis to the second derived image;

generate a synthesized image by synthesizing the target ultrasound image and the first and second adjusted derived images;

the synthesized image comprising an image component for smoothing and an image component for emphasizing a tissue structure generated based on the ultrasound image and first and second output images, the first and second output images being generated through a nonlinear image process, wherein the nonlinear image process is performed in at least one layer of multiresolution decomposition/reconstruction and includes an image filter which is set with a filter parameter for tissue smoothing and tissue boundary emphasis, the first output image is generated by applying the image filter which is set with the filter parameter calculated based on the ultrasound image in the nonlinear image process to the ultrasound image, the second output image is generated by applying the image filter which is set with the filter parameter having an arbitrary value to the ultrasound image, the image comprising an image component for smoothing is a subtraction image obtained from the ultrasound image and the second output image, and the image comprising an image component for emphasizing a tissue structure is a subtraction image obtained from the first output image and the second output image;

the ultrasonic diagnostic system further including input components each having a coordinate space of a number of dimensions corresponding to the number of the two derived images, wherein an adjustment parameter value is assigned to each axis of the coordinate space.

2. The ultrasonic diagnostic system of claim 1, wherein the image processing includes a nonlinear image filter using a diffusion equation, and the parameter is a parameter relating to a diffusion tensor of the diffusion equation.

3. The ultrasonic diagnostic system of claim 2, wherein the parameter is a size of an edge, the second output image is an output image of the image processing when the edge is zero, and the processing circuitry generates, as the two derived images, a first derived image which is a subtraction image of the target ultrasound image and the second output image, and a second derived image which is a subtraction image of the first output image and the second output image.

4. The ultrasonic diagnostic system of claim 2, wherein the first derived image of the two derived images includes an image component for smoothing, and the second derived image of the two derived images includes an image component for emphasizing a tissue structure.

5. The ultrasonic diagnostic system of claim 1, further including an input component for inputting the adjustment parameter value, for each adjustment parameter value for each of the two derived images.

6. The ultrasonic diagnostic system of claim 5, wherein the input components are either GUI components or mechanical components.

7. The ultrasonic diagnostic system of claim 1, further comprising a display device configured to display the input components which are GUI components, wherein the display device displays a text or a pictogram for explaining an adjustment parameter value corresponding to each of the input components.

8. The ultrasonic diagnostic system of claim 1, wherein the input components are either GUI components or mechanical components.

9. The ultrasonic diagnostic system of claim 8, wherein the adjustment parameter value varies depending on a depth position of each of the two derived images.

10. The ultrasonic diagnostic system of claim 1, wherein the adjustment parameter value varies depending on a spatial position of each of the two derived images.

11. The ultrasonic diagnostic system of claim 1, wherein each of the two derived images is on a spatial differential of a pixel value, a difference between pixel values, or edge information.

12. The ultrasonic diagnostic system of claim 1, further comprising: an ultrasound probe that transmits ultrasonic waves to the subject, receives reflected waves from the subject, and outputs echo signals in accordance with the reflected waves;

transmitter/receiver circuitry configured to convert the echo signals into reflected wave data in accordance with reception directivity; and B-mode processing circuitry configured to generate B-mode information based on the reflected wave data, wherein the processing circuitry generates the target ultrasound image based on the B-mode information.

13. An ultrasound image processing method comprising:

generating first and second derived images by applying a trained model to a target ultrasound image on a subject, the first derived image comprising a first image component for smoothing, the second derived image comprising a second image component for emphasizing a tissue structure, the trained model being a neural network trained to output, in response to input of an ultrasound image, an image comprising an image component for smoothing and an image comprising an image component for emphasizing a tissue structure;

inputting a variable first adjustment parameter value and a second adjustment parameter value corresponding to respective of the first and second derived images;

generating first and second adjusted derived images, the first adjusted derived image being generated by applying the variable first adjustment parameter value for adjusting a smoothing strength to the first derived, the second adjusted derived image being generated by applying the second adjustment parameter value for adjusting a strength of tissue boundary emphasis to the second derived image; and generating a synthesized image by synthesizing the target ultrasound image and the first and second adjusted derived images;

the synthesized image comprising an image component for smoothing and an image component for emphasizing a tissue structure are generated based on the ultrasound image and first and second output images, the first and second output images being generated through a nonlinear image process, including, performing in at least one layer of multiresolution decomposition/reconstruction and including image filtering in which an image filter which is set with a filter parameter for tissue smoothing and tissue boundary emphasis, generating the first output image by applying the image filter which is set with the filter parameter calculated based on the ultrasound image in the nonlinear image process to the ultrasound image, generating the second output image by applying the image filter which is set with the filter parameter having an arbitrary value to the ultrasound image, the image comprising an image component for smoothing is a subtraction image obtained from the ultrasound image and the second output image, and the image comprising an image component for emphasizing a tissue structure is a subtraction image obtained from the first output image and the second output image;

the method further including, defining input components each having a coordinate space of a number of dimensions corresponding to the number of the two derived images, and assigning an adjustment parameter value to each axis of the coordinate space.

14. An ultrasonic diagnostic system comprising:

processing circuitry configured to:

generate first and second derived images by applying a trained model to a target ultrasound image on a subject, the first derived image comprising a first image component for smoothing, the second derived image comprising a second image component for emphasizing a tissue structure, the trained model being a neural network trained to output, in response to input of an ultrasound image, an image comprising an image component for smoothing and an image comprising an image component for emphasizing a tissue structure;

input first and second adjustment parameter value corresponding to respective of the first and second derived images;

generate first and second adjusted derived images, the first adjusted derived image being generated by applying a variable first adjustment parameter value for adjusting a smoothing strength to the first derived image, the second adjusted derived image being generated by applying a second adjustment parameter value for adjusting a strength of tissue boundary emphasis to the second derived image;

generate a synthesized image by synthesizing the target ultrasound image and the first and second adjusted derived images;

the synthesized image comprising an image component for smoothing and an image component for emphasizing a tissue structure generated based on the ultrasound image and first and second output images, the first and second output images being generated through a nonlinear image process, wherein the nonlinear image process is performed in at least one layer of multiresolution decomposition/reconstruction and includes an image filter which is set with a filter parameter for tissue smoothing and tissue boundary emphasis, the first output image is generated by applying the image filter which is set with the filter parameter calculated based on the ultrasound image in the nonlinear image process to the ultrasound image, the second output image is generated by applying the image filter which is set with the filter parameter having an arbitrary value to the ultrasound image, the image comprising an image component for smoothing is a subtraction image obtained from the ultrasound image and the second output image, and the image comprising an image component for emphasizing a tissue structure is a subtraction image obtained from the first output image and the second output image;

the ultrasonic diagnostic system further including input components each having a coordinate space of a number of dimensions corresponding to the number of the two derived images, wherein an adjustment parameter value is assigned to each axis of the coordinate space, the nonlinear image process includes a nonlinear image filter using a diffusion equation, and the parameter is a size of an edge relating to a diffusion tensor of the diffusion equation, the second output image is an output image of the nonlinear image process when the edge is zero, and the processing circuitry generates, as the two derived images, a first derived image which is a subtraction image of the target ultrasound image and the second output image, and a second derived image which is a subtraction image of the first output image and the second output image.

15. An ultrasonic diagnostic method comprising:

generating first and second derived images by applying a trained model to a target ultrasound image on a subject, the first derived image comprising a first image component for smoothing, the second derived image comprising a second image component for emphasizing a tissue structure, the trained model being a neural network trained to output, in response to input of an ultrasound image, an image comprising an image component for smoothing and an image comprising an image component for emphasizing a tissue structure;

inputting first and second adjustment parameter values corresponding to respective of the first and second derived images;

generating first and second adjusted derived images, the first adjusted derived image being generated by applying a first adjustment parameter value, which is variable, for adjusting a smoothing strength to the first derived image, the second adjusted derived image being generated by applying the second adjustment parameter value for adjusting a strength of tissue boundary emphasis to the second derived image;

generate a synthesized image by synthesizing the target ultrasound image and the first and second adjusted derived images;

the synthesized image comprising an image component for smoothing and an image component for emphasizing a tissue structure generated based on the ultrasound image and first and second output images, the first and second output images being generated through a nonlinear image process, wherein the nonlinear image process is performed in at least one layer of multiresolution decomposition/reconstruction and includes an image filter which is set with a filter parameter for tissue smoothing and tissue boundary emphasis, the first output image is generated by applying the image filter which is set with the filter parameter calculated based on the ultrasound image in the nonlinear image process to the ultrasound image, the second output image is generated by applying the image filter which is set with the filter parameter having an arbitrary value to the ultrasound image, the image comprising an image component for smoothing is a subtraction image obtained from the ultrasound image and the second output image, and the image comprising an image component for emphasizing a tissue structure is a subtraction image obtained from the first output image and the second output image;

wherein the diagnostic method further comprises, defining input components each having a coordinate space of a number of dimensions corresponding to the number of the two derived images, assigning an adjustment parameter value to each axis of the coordinate space, the nonlinear image process includes a nonlinear image filter using a diffusion equation, and the parameter is a size of an edge relating to a diffusion tensor of the diffusion equation, the second output image is an output image of the nonlinear image process when the edge is zero, and generating, as the two derived images, a first derived image which is a subtraction image of the target ultrasound image and the second output image, and a second derived image which is a subtraction image of the first output image and the second output image.

* * * * *